(12) United States Patent
Meng et al.

(10) Patent No.: US 9,816,667 B2
(45) Date of Patent: Nov. 14, 2017

(54) LUBRICANT, FRICTION PAIR HAVING THE LUBRICANT AND METHOD FOR CONTROLLING FRICTION COEFFICIENT BETWEEN THE FRICTION PAIR

(71) Applicant: Tsinghua University, Beijing (CN)

(72) Inventors: Yonggang Meng, Beijing (CN); Xiaoyong Yang, Beijing (CN); Yu Tian, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 21 days.

(21) Appl. No.: 14/759,220

(22) PCT Filed: Jan. 6, 2014

(86) PCT No.: PCT/CN2014/070153
§ 371 (c)(1),
(2) Date: Jul. 3, 2015

(87) PCT Pub. No.: WO2014/106484
PCT Pub. Date: Jul. 10, 2014

(65) Prior Publication Data
US 2015/0330565 A1  Nov. 19, 2015

(30) Foreign Application Priority Data
Jan. 5, 2013  (CN) .......................... 2013 1 0002692

(51) Int. Cl.
*F16N 29/00* (2006.01)
*F16N 15/00* (2006.01)
(Continued)

(52) U.S. Cl.
CPC ........... *F16N 29/00* (2013.01); *C10M 169/04* (2013.01); *C10M 177/00* (2013.01); *F16N 15/00* (2013.01);
(Continued)

(58) Field of Classification Search
CPC ...... F16N 29/00; F16N 15/00; C10M 169/04; C10M 177/00; G01N 33/2888
(Continued)

(56) References Cited

U.S. PATENT DOCUMENTS 4,560,601 A * 12/1985 Datta ................... C10M 169/04
369/276
2006/0089276 A1 * 4/2006 Klotz ...................... C08J 7/047
508/464
(Continued)

FOREIGN PATENT DOCUMENTS

| CN | 1197107 A | 10/1998 |
| CN | 102102805 A | 6/2011 |
| CN | 103075628 A | 5/2013 |

*Primary Examiner* — Michael Riegelman
(74) *Attorney, Agent, or Firm* — Kile Park Reed & Houtteman LLC

(57) ABSTRACT

A lubricant, a friction pair having the lubricant and a method for controlling COF between the friction pair are provided. The friction pair includes a first friction part (1) and a second friction part (2). Firstly a lubricant (4) is provided between the first and second friction parts (1, 2). Then a potential is applied on the first friction part (1) via the lubricant (4). And COF is controlled by controlling the potential. The lubricant (4) contains propylene carbonate and a surfactant.

6 Claims, 8 Drawing Sheets

(51) Int. Cl.
*G01N 33/28* (2006.01)
*C10M 169/04* (2006.01)
*C10M 177/00* (2006.01)

(52) U.S. Cl.
CPC ... *G01N 33/2888* (2013.01); *C10M 2207/126* (2013.01); *C10M 2207/325* (2013.01); *C10M 2219/042* (2013.01); *C10M 2219/044* (2013.01); *C10N 2210/01* (2013.01); *C10N 2230/02* (2013.01); *C10N 2230/60* (2013.01); *C10N 2240/02* (2013.01); *F16N 2250/42* (2013.01); *Y10T 74/19991* (2015.01)

(58) Field of Classification Search
USPC .......................................... 184/6.12
See application file for complete search history.

(56) References Cited

U.S. PATENT DOCUMENTS

| | | | |
|---|---|---|---|
| 2007/0039378 A1* | 2/2007 | Wollenberg | G01N 33/2888 73/53.05 |
| 2007/0139862 A1* | 6/2007 | Tateishi | H01G 9/038 361/502 |
| 2013/0313160 A1* | 11/2013 | Wigand | E21B 43/16 208/19 |
| 2014/0106994 A1* | 4/2014 | Furukawa | C10M 169/04 508/126 |

* cited by examiner

LUBRICANT, FRICTION PAIR HAVING THE LUBRICANT AND METHOD FOR CONTROLLING FRICTION COEFFICIENT BETWEEN THE FRICTION PAIR

CROSS-REFERENCE TO RELATED APPLICATION

This U.S. application claims priority under 35 U.S.C 371 to, and is a U.S. National Phase application of, the International Patent Application No. PCT/CN2014/070153, filed Jan. 6, 2014, which claims the benefit of prior Chinese Application No. 201310002692.9 filed Jan. 5, 2013. The entire contents of the before-mentioned patent applications are incorporated by reference as part of the disclosure of this U.S. application.

FIELD

The present disclosure relates to the field of mechatronics, and more particularly to a lubricant, a friction pair having the lubricant, and a method for controlling a friction coefficient between the friction pair.

BACKGROUND

Friction and wear are two main problems encountered during the operation of a machine. The friction is mainly influenced by the material of the friction pair, lubricating state, speed, load and so on. In practice, increasing researches have been made on the friction, and various techniques for utilizing or inhibiting the friction have been invented accordingly, for example, belt drive, rolling bearing, etc. These techniques are capable of controlling the friction passively, and the friction features of related friction components may be predetermined by specific designs and productions before use.

In the application of friction clutch, friction force of the friction parts should always been controlled during running. As passive friction controlling technique cannot fulfill the above requirements, it needs to develop an active friction controlling technique. Lots of researches have been made on the online active friction controlling technique, especially for the friction controlling technique based on an external electrical field. However, various problems still need to be solved. For example, the metal friction part is easy to corrode in the case that the lubricant is in the form of aqueous solution. When the friction is electrically controlled through an electro-chemical reaction, the metal friction part is corroded continuously due to the electro-chemical reaction. Further, when the external voltage applied on the lubricant is as high as 10-20 V, hydrogen evolution can occur in the solution. In this condition, the lubricant is significantly consumed. In the case that the lubricant is an aqueous surfactant solution, the metal friction part is easy to corrode because of immersing in the surfactant solution for a long time.

Conventional friction control techniques based on external electrical field are all limited for the reasons listed above. Currently, it is highly needed for a lubricant and a friction controlling method, which may be used in a friction controlling technique, and which are able to reduce or even avoid the corrosion of metal friction parts and may be applied within a wide load-speed range, so that requirements for the mechanical engineering can be satisfied.

SUMMARY

Embodiments of the present disclosure seek to solve at least one of the problems existing in the prior art to at least some extent, or to provide a consumer with a useful commercial choice.

Embodiments of a first broad aspect of the present disclosure provide a method for controlling a friction coefficient between a friction pair. The friction pair includes a first friction part and a second friction part. The method may include: providing a lubricant between the first and second friction parts; applying a potential on the first friction part via the lubricant; and controlling the friction coefficient by controlling the potential. The lubricant may contain propylene carbonate and a surfactant.

In some embodiments, the surfactant may contain at least one selected from a group consisting of: cationic surfactant, anionic surfactant and zwitterionic surfactant.

The inventors have surprisingly found, the method according to embodiments of the present disclosure is easy to operate and convenient for use. In addition, the method may be applied within wide load and speed ranges, and electro-chemical corrosion of the first and second friction parts of the friction pair may be reduced or delayed efficiently or even avoided. In addition, with the method according to embodiments of the present disclosure, the friction coefficient may be controlled efficiently, safely and precisely. Thereby, the method according to embodiments of the present disclosure may be applied in the friction clutch field, in which the friction needs to be controlled online actively.

In some embodiments, the surfactant may contain at least one selected from a group consisting of: sodium dodecyl sulfate, sodium oleate, sodium stearate and sodium dodecyl sulfonate.

In some embodiments, the lubricant may be a solution containing the sodium dodecyl sulfate and the propylene carbonate.

In some embodiments, the sodium dodecyl sulfate may have a concentration selected from: 0.1 mM, 0.5 mM, 1 mM and 2 mM.

In one embodiment, the solution refers to a propylene carbonate fluid containing the propylene carbonate, and the sodium dodecyl sulfate has a concentration of 0.1 mM, 0.5 mM, 1 mM or 2 mM. It is to be noted that, in this solution, the sodium dodecyl sulfate is the solute while the propylene carbonate fluid is the solvent.

In some embodiments, the method may further include subjecting the lubricant to an ultrasonication at a temperature ranging from about 40° C. to about 50° C. In one embodiment, the ultrasonication may be carried out before providing the lubricant between the first and second friction parts.

In some embodiments, the first friction part may be made of metal.

In some embodiments, the second part may be made of metal.

In some embodiments, the second part may be made of ceramic.

In some embodiments, the potential may be applied on the first friction part via an electrode system. The electrode system may include: a working electrode; a counter electrode made from inert material and adapted to provide a current channel for the working electrode; and a reference electrode adapted to provide a potential channel for the working electrode. The first friction part is used as the working electrode. Thereby, the friction coefficient may be controlled online actively and efficiently by controlling the potential of the working electrode, i.e. the first friction part.

Embodiments of a second broad aspect of the present disclosure provide a lubricant. The lubricant may contain propylene carbonate and a surfactant.

In some embodiments, the surfactant may contain at least one selected from a group consisting of: cationic surfactant, anionic surfactant and zwitterionic surfactant.

The lubricant according to embodiments of the present disclosure may be applied in the friction controlling in order to control the friction coefficient between the friction pair. In addition, with the lubricant, the method may be applied within wide load and speed ranges, and electro-chemical corrosion of the first and second friction parts may be reduced or delayed efficiently or even avoided.

In an embodiment of the present disclosure, the lubricant may be disposed between the first and second friction parts, thus the friction coefficient may be controlled efficiently by controlling the potential of the first friction part (i.e. the working electrode). What is more, the lubricant according to embodiments of the present disclosure is more stable, and the metal friction part (for example, the first friction part) may have a wider electro-chemical stable potential window. Further, when controlling the friction electrically with the lubricant according to embodiments of the present disclosure, the potential of the working electrode may be adjusted in a wider range. What is more, the lubricant may facilitate to delay or reduce or even avoid the corrosion of the metal friction parts (such as the first and second friction parts), so that the friction pair may have a longer service life.

In some embodiments, the surfactant may contain at least one selected from a group consisting of: sodium dodecyl sulfate, sodium oleate, sodium stearate and sodium dodecyl sulfonate.

In some embodiments, the lubricant may be a solution containing the sodium dodecyl sulfate and the propylene carbonate.

In some embodiments, the sodium dodecyl sulfate may have a concentration selected from: 0.1 mM, 0.5 mM, 1 mM and 2 mM.

Embodiments of a third broad aspect of the present disclosure provide a friction pair. The friction pair may include: a first friction part, a second friction part; and a lubricant described above and provided between the first and second friction parts.

The inventors have surprisingly found that, the friction coefficient between the friction pair may be easy to control, and the first and second friction parts may be hard to corrode by an electro-chemical reaction. The friction pair may be safe to use and have a long service life. In addition, the friction pair may be applied within wide load and speed ranges, therefore the friction pair may be widely applied in various fields, such as the friction clutch field, in which the friction needs to be controlled online actively.

Advantages of the lubricant, the friction pair having the lubricant, and the method for controlling the friction coefficient according to embodiments of the present disclosure will be described as follows, for a better understanding of the present disclosure.

1) The lubricant according to embodiments of the present disclosure may be used to electrically control the friction between the friction pair. In comparison with a conventional aqueous surfactant solution, the lubricant according to embodiments of the present disclosure is more stable, and the electro-chemical stable potential window of the lubricant is wider. Further, the electro-chemical corrosion of metal friction parts (for example, the first and second friction parts) during the controlling process may be delayed, reduced or even avoided. Therefore, the lubricant according to embodiments of the present disclosure has wider application areas.

2) With the method according to embodiments of the present disclosure, the friction characteristics (for example, the friction coefficient) may be controlled online actively by controlling the potential applied on the first friction part (i.e. the working electrode). The potential of the working electrode is restricted within the electro-chemical stable potential window of the working electrode, therefore the electro-chemical corrosion of the metal friction parts may be avoided efficiently. In addition, the method may use the lubricant containing the propylene carbonate and the surfactant, in which the concentration of the propylene carbonate may reach 2 mM. The metal friction part which can be immersed in the lubricant without significant corrosion may have a wider electro-chemical stable potential window, and the potential of the working electrode may be adjusted within a wide potential range, such as from about −1.5V to about +1.5V. In this way, with the method and lubricant according to embodiments of the present disclosure, the friction coefficient may be controlled precisely.

3) With the method according to embodiments of the present disclosure, the shortest period that the friction coefficient cost to reach a stable potential value (when changing within a potential section) may be smaller than 10 seconds. Further, the friction coefficient may have a better sustainability, for example, the friction coefficient may change by up to 200% due to the change of the potential. Therefore, various requirements in the electronically controlled friction areas may be well satisfied.

4) The method according to embodiments of the present disclosure may be applied within a very wide load-speed range, for example, a load up to 400 N and a speed up to 100 rpm. Therefore, various requirements in the electronically controlled friction areas may be well satisfied.

5) The method according to embodiments of the present disclosure may be easy to operate and convenient for use, and may be used to control the friction coefficient precisely. Therefore the method may be applied in a plurality of fields, such as the friction clutch field, in which friction needs to be controlled online actively.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
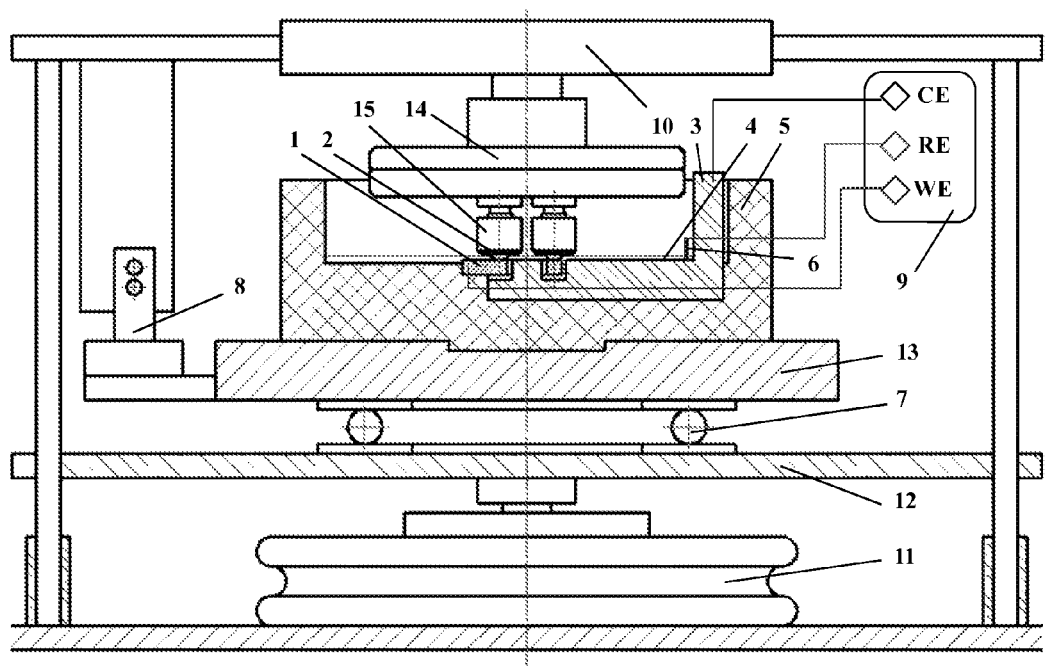
FIG. 1 is a cross-sectional view showing a device operated with the method for controlling the friction coefficient between a friction pair according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar parts and the parts having same or similar functions are denoted by like reference numerals throughout the descriptions.

In the specification, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation.

Terms concerning attachments, coupling and the like, such as "connected" and "interconnected", refer to a relationship in which structures are secured or attached to one another either directly or indirectly through intervening structures, as well as both movable or rigid attachments or relationships, unless expressly described otherwise.

In addition, terms such as "first" and "second" are used herein for purposes of description and are not intended to indicate or imply relative importance or significance.

For the purpose of the present description and of the following claims, the definitions of the numerical ranges always include the extremes unless otherwise specified.

Embodiments of the first aspect of the present disclosure provide a method for controlling the friction coefficient (COF) between a friction pair, in which the friction pair includes a first friction part and second friction part. The method may include the following steps.

Step S100: a lubricant is provided between the first and second friction parts;

Step S200: a potential is applied on the first friction part via the lubricant; and Step S300: COF is controlled by controlling the potential.

The inventors have surprisingly found that, with the method according to embodiments of the present disclosure, COF between the friction pair may be controlled efficiently and precisely. In addition, in the method, a lubricant which is electro-chemically stable may be disposed between the first and second friction parts, so that metal friction parts (such as the first or second friction part) of the friction pair may have a wider electro-chemical stable potential window. In this way, electro-chemical corrosion may be avoided efficiently. Further, the method may be easy to operate and convenient for use, may be applied within a wide load-speed range. Therefore, the method according to embodiments of the present disclosure may be applied in various fields, such as the friction clutch, in which the friction needs to be controlled online actively. With the method according to embodiments of the present disclosure, COF may be controlled efficiently, safely and precisely.

Figure 16:
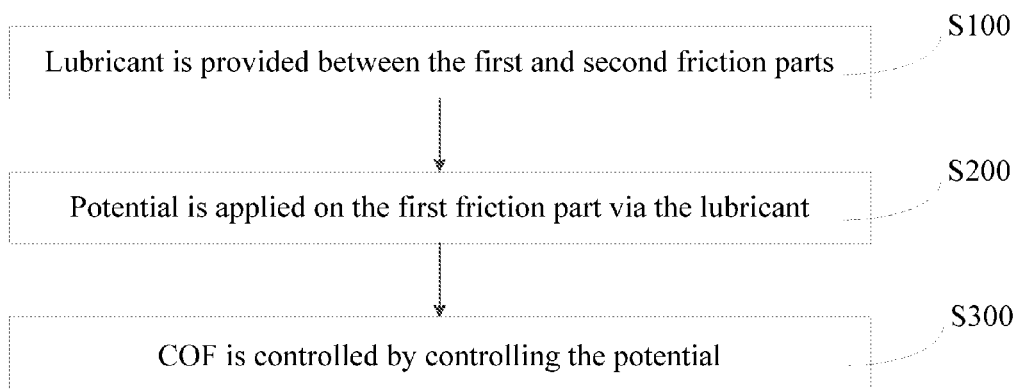
FIG. 16 is a flow chart showing a method for controlling the friction coefficient between the friction pair according to an embodiment of the present disclosure.

The method for controlling COF according to embodiments of the present disclosure will be explained in details in the following with reference to FIG. 16.

Providing Lubricant

In the step S100: the lubricant is provided between the first and second friction parts.

In some embodiments, the first friction part may be made of metal.

The material of the second metal part is not limited in the present disclosure. In some embodiment, the second part may be made of metal. In some embodiment, the second part may be made of ceramic. Therefore, COF between the friction pair may be controlled efficiently and precisely.

In some embodiments, the lubricant may contain propylene carbonate and a surfactant.

There are no particular limits for the surfactant in embodiments of the present disclosure, for example, the surfactant may contain at least one selected from a group consisting of: cationic surfactant, anionic surfactant and zwitterionic surfactant. Therefore, electro-chemical corrosion in the metal friction part of the friction part may be delayed, reduced or even avoided. In addition, with the method, the load and speed ranges applied in the electrically controlled friction technique may be significantly broadened.

There are no particular limits for the types of the surfactant in the present disclosure. In some embodiments, the surfactant may contain at least one selected from a group consisting of: sodium dodecyl sulfate, sodium oleate, sodium stearate and sodium dodecyl sulfonate. In one embodiment, the surfactant is sodium dodecyl sulfate.

In some embodiments, the lubricant may be a solution containing the sodium dodecyl sulfate and the propylene carbonate. In other words, the lubricant may be a propylene carbonate containing the sodium dodecyl sulfate.

In some embodiments, the sodium dodecyl sulfate may have a concentration selected from: 0.1 mM, 0.5 mM, 1 mM and 2 mM, based on the lubricant.

With the lubricant described above, COF may be controlled more efficiently and precisely.

Applying Potential

In the step S200: the potential is applied on the first friction part via the lubricant.

In some embodiments, the lubricant may be subjected to an ultrasonication at a temperature ranging from about 40° C. to about 50° C., prior to the step S200. Thereby, the surfactant (act as the solute) may be dissolved in the propylene carbonate solution (act as the solvent) completely, so as to facilitate the precise control of COF between the friction pair. Ultrasonication is known to those skilled in the art, so details related to this technique are omitted herein.

In some embodiments, the potential may be applied on the first friction part by an electrode system. The electrode system may include a working electrode, a counter electrode and a reference electrode. In an embodiment, the first friction part is used as the working electrode. The counter electrode may be made from inert material and adapted to provide a current channel for the wording electrode (i.e. the first friction part). The reference electrode may be adapted to provide a potential channel for the working electrode. Thereby, by means of controlling the potential of the working electrode, COF may be controlled online actively.

Controlling Potential

In the step 300, COF is controlled by controlling the potential applied on the first friction part.

In some embodiments, firstly the potential of the working electrode is adjusted to a predetermined value, then COF may change continuously in the beginning, and finally may reach a stable value. When the potential is changed, COF may change accordingly. Those with ordinary skill in the art will appreciate, when the potential applied on the working electrode is changed, the lubricant adsorbed on the surface of the working electrode (lubricants covered on the surface of the first friction part) may subject to a molecular rearrangement. In this condition, molecular arrangement and molecular density of the lubricant may be changed, so that lubricating characteristics of the lubricant may be changed, thus causing the change of COF.

Embodiments of the second aspect of the present disclosure provide a lubricant, the lubricant is adapted to apply between the first and second friction parts described above. The lubricant may contain propylene carbonate and a surfactant.

There are no particular limits for the surfactant in embodiments of the present disclosure, for example, the surfactant may contain at least one selected from a group consisting of: cationic surfactant, anionic surfactant and zwitterionic surfactant.

There are no particular limits for the types of the surfactant in the present disclosure. In some embodiments, the surfactant may contain at least one selected from a group consisting of: sodium dodecyl sulfate, sodium oleate, sodium stearate and sodium dodecyl sulfonate. In one embodiment, the surfactant is sodium dodecyl sulfate.

In some embodiments, the lubricant may be a solution of sodium dodecyl sulfate in propylene carbonate. In other words, the solution may be a propylene carbonate solution containing sodium dodecyl sulfate.

In some embodiments, the sodium dodecyl sulfate may have a concentration selected from: 0.1 mM, 0.5 mM, 1 mM and 2 mM, based on the lubricant.

Therefore, when the above method is operated with the lubricant, COF may be controlled more efficiently and precisely.

The inventors have surprisingly found that, the lubricant according to embodiments of the present disclosure may be applied in the electrically controlled friction technique, in which COF needs to be controlled. In addition, the lubricant may be applied within wide load and speed ranges. With the lubricant, the electro-chemical corrosion may be delayed, reduced or even avoided, so that the service life of the friction pair may be prolonged.

Embodiments of the third aspect of the present disclosure provide a friction pair. The friction pair may include: a first friction part, a second friction part and a lubricant disposed between the first and second friction parts.

The inventors have surprisingly found that, with the friction pair according to embodiments of the present disclosure, COF may be easy to control, and the metal friction part may be hard to corrode. The friction pair is safe, has a long service life, and may be applied within wide load and speed ranges, thus may be applied widely in various areas, such the friction clutch, in which the friction needs to be controlled online actively.

A device operated with the method for controlling COF between the friction pair according to embodiments of the present disclosure may be described in the following, for a better understanding of the present disclosure.

As shown in FIG. 1, the device 1000 include: a friction pair including a first friction part 1 and a second friction part 2, a counter electrode 3, a lubricant 4, a lubricating pool 5, a reference electrode 6, a thrust ball bearing 7, a force sensor 8, a potentiostat 9, a speed regulating system 10, a loading unit 11, a lifting table 12, a base 13, a coupling 14 and a clamp 15.

In some embodiments, the first friction part 1 is made of metal and act as a working electrode, and the second friction part 2 may be made of metal or ceramic.

As shown in FIG. 1, in an embodiment, the first friction part 1 is a stainless steel disc, which is arranged in the lubricating pool 5 through a spline groove (not shown). The second friction part 2 is made of zirconium dioxide ($ZrO_2$), which is fixed within the clamp 15 and forms a point contact with the first friction part 1. The lubricant 4 is dispersed within the lubricating pool 5, and the friction pair including the first and second friction parts 1, 2 is immersed in the lubricant 4 in order to lubricate the friction pair. The lubricating pool 5 is mounted on the lift table 12 via the base 13 and the thrust ball bearing 7. The load unit 11 is an air cushion, which is located below the lift table 12 and connects with the friction pair via the lift table 12, the thrust ball bearing 7, the base 13 and the lubricating pool 5. The force sensor 8 is located above the lift table 12 and fixed adjacent to the base 13.

Figure 2:
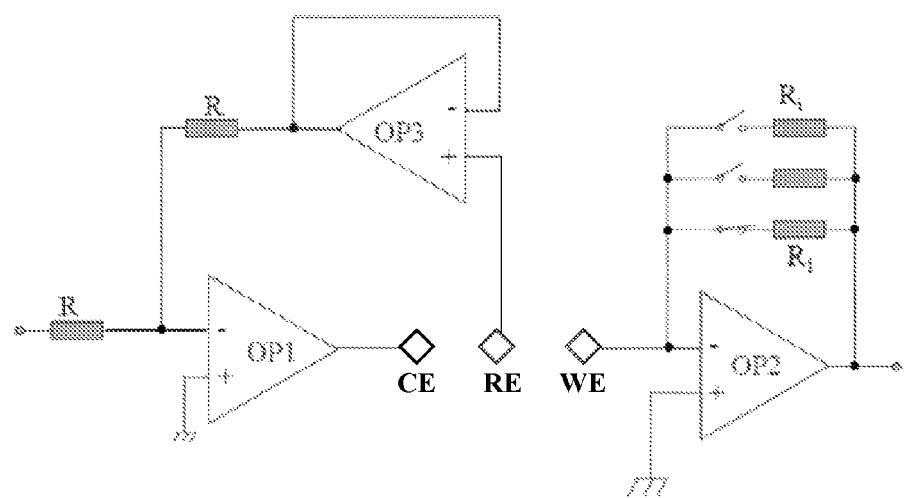
FIG. 2 shows a circuit diagram of a potentiostat 9 illustrated in FIG. 1.

In the present embodiment, the electrode system may include: the working electrode (i.e. the first friction part 1), the counter electrode 3 and the reference electrode 6. The counter electrode 3 is a graphite electrode, which is fixed within the lubricating pool 5 through a screw-thread and adjacent to the first friction part 1. In one embodiment, the distance between the counter electrode 3 and the first friction part 1 may be about 1 mm. The lubricant 4 may fill the gap formed between the first friction part 1 and the counter electrode 3. The reference electrode 6 is silver/silver chloride (Ag/AgCl) solid electrode, which is arranged adjacent to the friction pair. In addition, the potentiastat 9 may be a PGSTAT302N potentiostat commercially available from Metrohm Autolab. The working electrode, counter electrode 3 and reference electrode 6 may connected with the potentiastat 9 via corresponding connecting wires. The working principle of the potentiostat 9 is illustrated with reference to FIG. 2. As shown in FIG. 2, WE indicates the working electrode 1, CE indicates the counter electrode 3, RE indicates the reference electrode 6, OP indicates an operational amplifier, and R indicates a resistance.

The method for controlling COF embodied with the device described above will be explained in details below.

Firstly, by means of closed-loop control, a predetermined normal load is applied on the metal friction pair through the loading unit 11 by air. Then, by means of closed-loop control, a predetermined rotating speed is provided to the friction air by the speed regulating system 10. A first force detected by the force sensor 8 and a second force applied on the rotating center of the friction pair (the friction force) are a pair of balance forces, so the friction force may be calculated by the balance relationship. COF is expressed as the ratio of the friction force to the normal load. The lubricant 4 may act as the electrolyte between the counter electrode 3 and the working electrode. The reference electrode 6 may provide a potential channel for the working electrode, and the counter electrode 3 may provide a current channel for the working electrode. The potentiastat 9 may be used to control or adjust the potential of the working electrode precisely, therefore COF may be controlled or adjusted online actively and precisely.

In some embodiments, the electro-chemical stable potential window of the working electrode in the lubricant 4 may be detected and determined by the potentiastat 9 by means of cyclic voltammetry (CV). The electro-chemical stable potential window may be the potential range acceptable to the working electrode, therefore the electro-chemical corrosion of the first friction part 1 may be reduced efficiently or even avoided.

Figure 4:
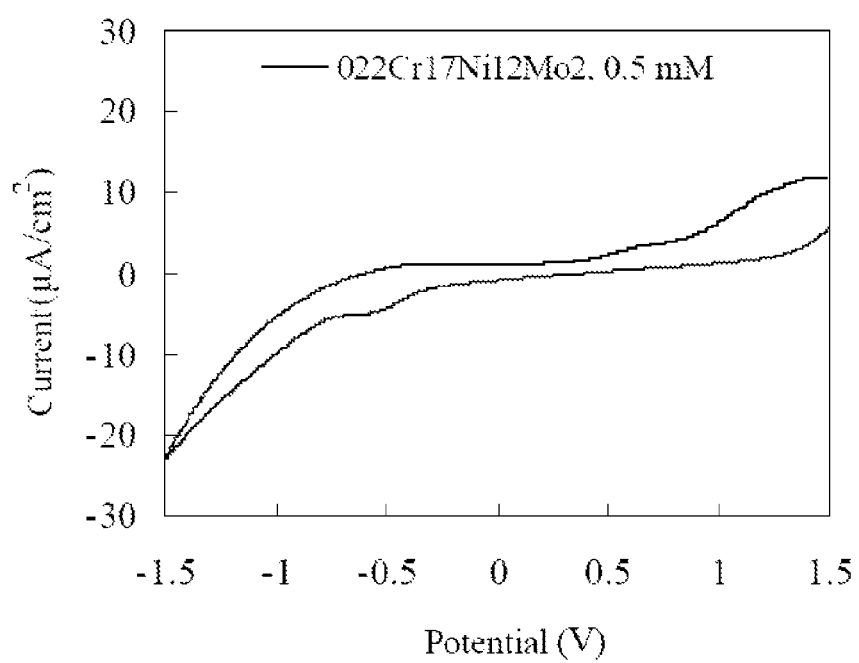

Specifically, the first friction part 1 may be a stainless steel disc (No. 4Cr13), and the lubricant 4 is the propylene carbonate solution containing sodium dodecyl sulfate, and the sodium dodecyl sulfate has a concentration of about 2 mM. The electro-chemical stable potential window of the first friction part 1 may range from about −1.5 V to about +1.5 V (as shown in FIG. 4).

Figure 3:
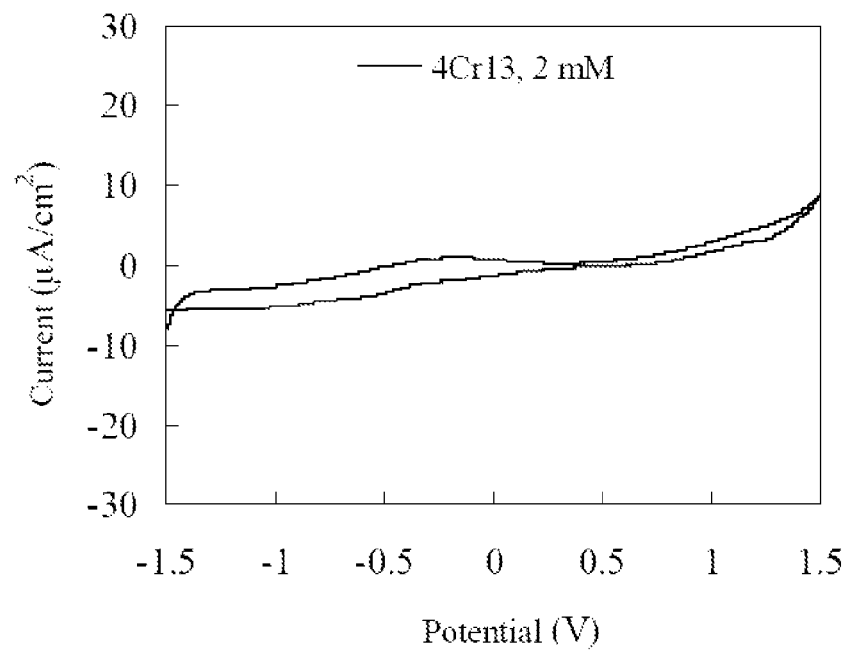
FIGS. 3 and 4 show curves illustrating the relationship between the current and the potential of the working electrode according to an embodiment of the present disclosure.

In some embodiments, the first friction part 1 is the stainless steel disc (No. 4Cr13), and the lubricant is the propylene carbonate solution containing sodium dodecyl sulfate, and the sodium dodecyl sulfate has a concentration of about 2 mM. In some embodiments, the first friction part 1 is the stainless steel disc (No. 022Cr17Ni12Mo2), and the lubricant is the propylene carbonate solution containing sodium dodecyl sulfate, and the concentration of the sodium dodecyl sulfate is not more than 0.5 mM. In this way, the potential of the working electrode may be well adjusted or controlled within the electro-chemical stable potential window, for example, in the range from about −1.5 V to about +1.5 V, while the metal friction part 1 may not be electro-chemically corroded. In addition, as shown in FIGS. 3-4, the potential of the first metal friction part 1 are all determined in relative to the reference electrode 3, i.e. Ag/AgCl electrode.

Additional aspects and advantages of the embodiments of the present disclosure will be given in part in the following descriptions, become apparent in part from the following descriptions, or be learned from the practice of the embodiments of the present disclosure.

The person skilled in the art will appreciate that, those devices, techniques and operating conditions which are not specifically described in the following embodiments are known in related art, and will be embodied according to various references and articles in the art. The reactants or devices may be commercially available. It is to be noted that, in the following embodiments, the potential of the first friction part 1 is described with reference to the reference electrode (i.e. Ag/AgCl electrode).

Embodiment 1

The method for controlling COF between the friction pair was carried out according to embodiments described above and was operated with the device shown in FIG. 1, and the relationship between COF and the potential of the first friction part 1 (working electrode) was detected. In the present embodiment, the first friction part 1 was a stainless steel disc (4Cr13), the second friction part 2 was two $ZrO_2$ balls having the same rotating radius, and the lubricant 4 was a propylene carbonate solution containing sodium dodecyl sulfate.

Figure 5:
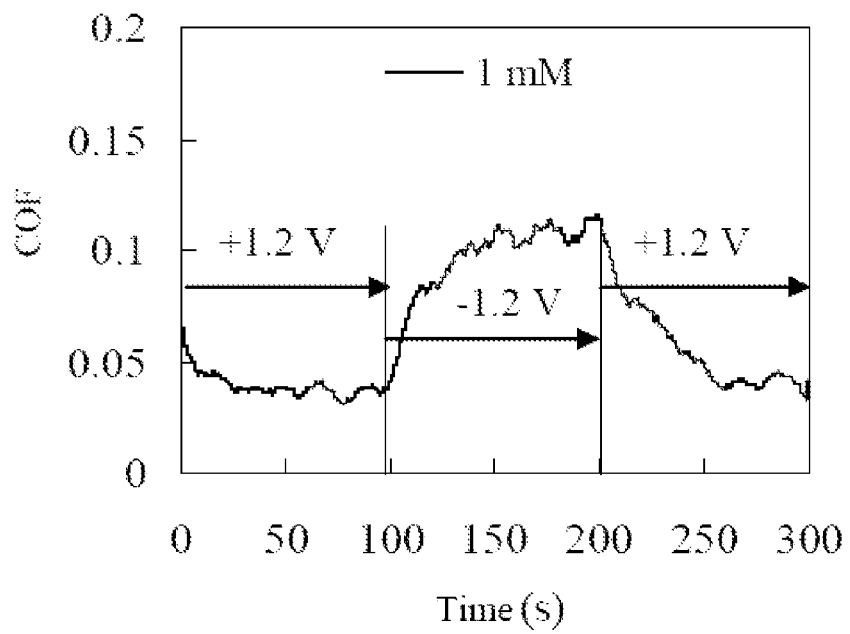
FIGS. 5 and 6 show curves illustrating the relationship between the potential of the working electrode and the friction coefficient according to an embodiment of the present disclosure.
Figure 6:
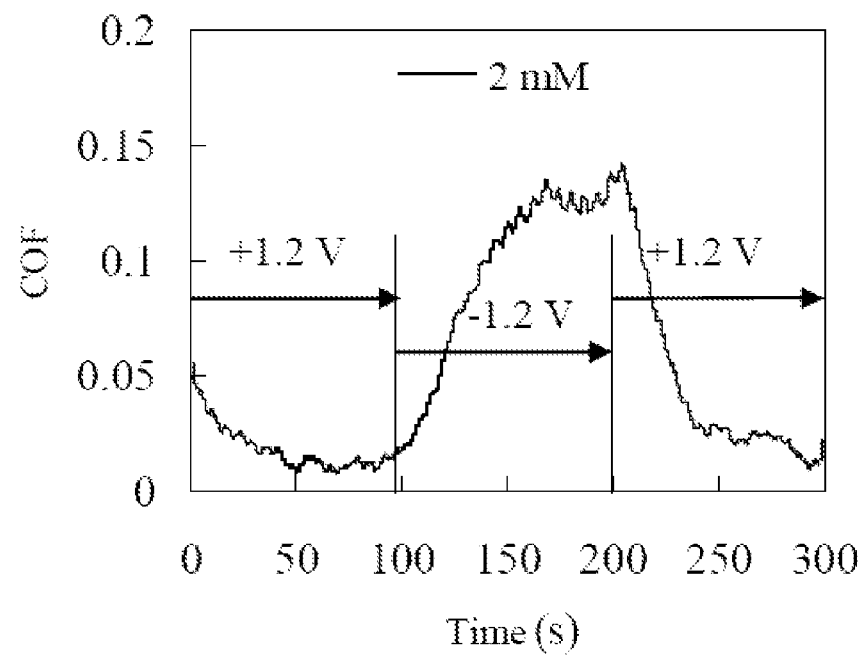

In the present embodiment, it was detected how COF was changing with the change of the potential of the first friction part 1, thus COF would be controlled. Specifically, FIGS. 5 and 6 show curves illustrating how COF is changing with the change of the potential of the first friction part 1. In the embodiment as shown in FIG. 5, the operating condition was as follows: a normal load of the friction pair was 50 N, a rotating speed of the friction pair was 10 rpm, a concentration of the sodium dodecyl sulfate was 1 mM based on the lubricant 4. In the embodiment as shown in FIG. 6, the operating condition was as follows: a normal load of the friction pair was 50 N, a rotating speed of the friction pair was 10 rpm, a concentration of the sodium dodecyl sulfate was 2 mM based on the lubricant 4.

Referring to FIGS. 5 and 6, the potential of the first friction part 1 changed with the rule of: +1.2 V→−1.2 V→+1.2 V. With the change of the potential, COFs in FIGS. 5 and 6 show the same changing rule: COF decreases when the potential is changing in the positive potential step (such as +1.2 V); and COF increases when the potential is changing in the negative potential step (such as −1.2 V).

As described above, with the method according the embodiment of the present disclosure, COF between the friction pair may be controlled efficiently, in addition, when the lubricant contains anionic surfactant, it is indicated that: COF may decrease when the potential of the working electrode is in the positive potential step; and COF may increase when the potential of the working electrode is in the negative potential step.

Embodiment 2

The method for controlling COF between the friction pair was carried out according to embodiments described above and was operated with the device shown in FIG. 1, and the relationship between COF and the potential of the first friction part 1 (working electrode) was detected. In the present embodiment, the first friction part 1 was a stainless steel disc (4Cr13), the second friction part 2 was three $ZrO_2$ balls having the same rotating radius, and the lubricant 4 was a propylene carbonate solution containing sodium dodecyl sulfate.

Figure 7:
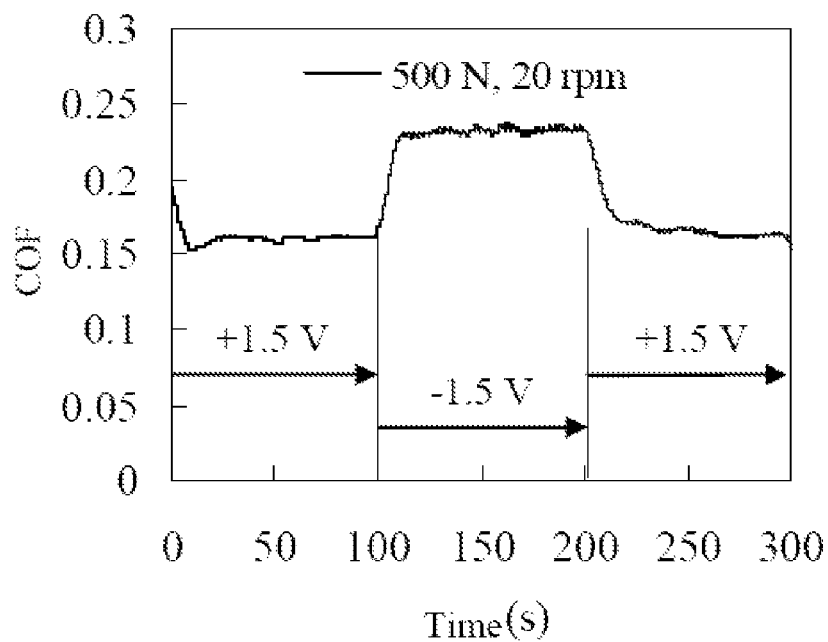
FIGS. 7-9 show curves illustrating the relationship between the potential of the working electrode and the friction coefficient according to another embodiment of the present disclosure.
Figure 8:
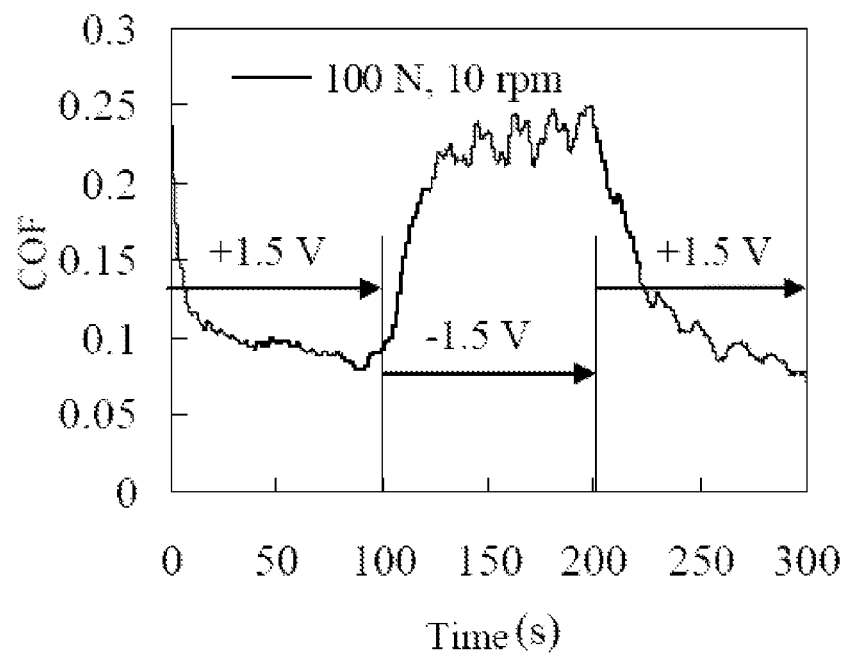
Figure 9:
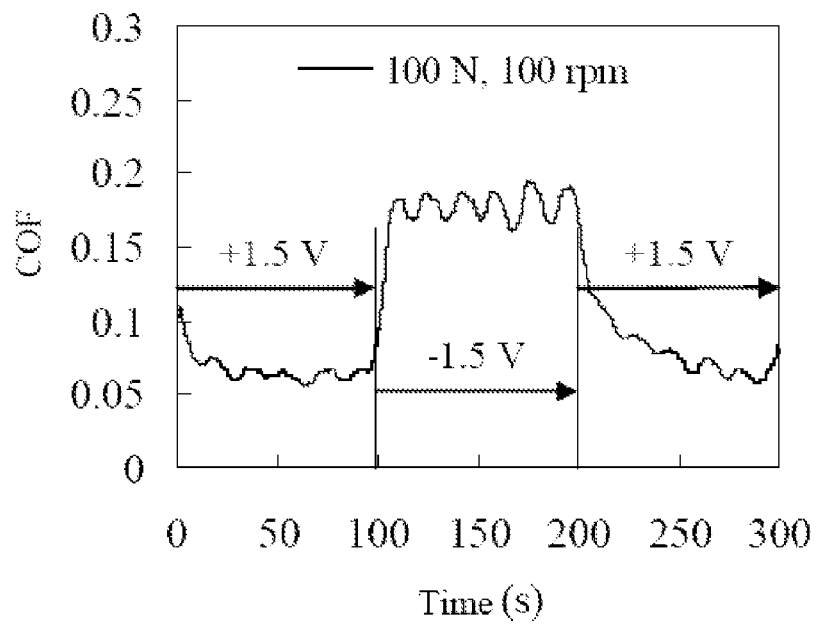

FIGS. 7-9 show curves illustrating how COF is changing with the change of the potential of the first friction part 1. In the embodiment as shown in FIG. 7, the operating condition was as follows: a normal load of the friction pair was 500 N, a rotating speed of the friction pair was 20 rpm, a concentration of the sodium dodecyl sulfate was 1 mM based on the lubricant 4. In the embodiment as shown in FIG. 8, the operating condition was as follows: a normal load of the friction pair was 100 N, a rotating speed of the friction pair was 10 rpm, a concentration of the sodium dodecyl sulfate was 1 mM based on the lubricant 4. In the embodiment as shown in FIG. 9, the operating condition was as follows: a normal load of the friction pair was 100 N, a rotating speed of the friction pair was 100 rpm, a concentration of the sodium dodecyl sulfate was 1 mM based on the lubricant 4.

Referring to FIGS. 7-9, the potential of the first friction part 1 changes with the rule of: +1.5 V→−1.5 V→+1.5 V. At each potential changing position, COF changes continuously initially, then reaches a stable potential value and maintains at this potential value in the remaining period of this potential. With the change of the potential, it costs about 5 seconds to about 20 seconds for the potential to reach the stable potential value. With the potential change within the range of +1.5 V→1.5 V, COF may change by 60% to 200%.

As described above, with the method according the embodiment of the present disclosure, the shortest time the potential takes to reach the stable potential value is no more than 10 seconds, and COF may have a better sustainability under a constant potential. In addition, COF may change by up to 200%, thus COF may be controlled efficiently and precisely. In this way, requirements need to be met in the electrically controlled friction field may be well satisfied.

Embodiment 3

The method for controlling COF between the friction pair was carried out according to embodiments described above and was operated with the device shown in FIG. 1, and the relationship between COF and the potential of the first friction part 1 (working electrode) under different lubricant concentrations was detected. In the present embodiment, the first friction part 1 was a stainless steel disc (022Cr17Ni12Mo2), the second friction part 2 was one $ZrO_2$ ball, and the lubricant 4 was a propylene carbonate solution containing sodium dodecyl sulfate.

Figure 10:
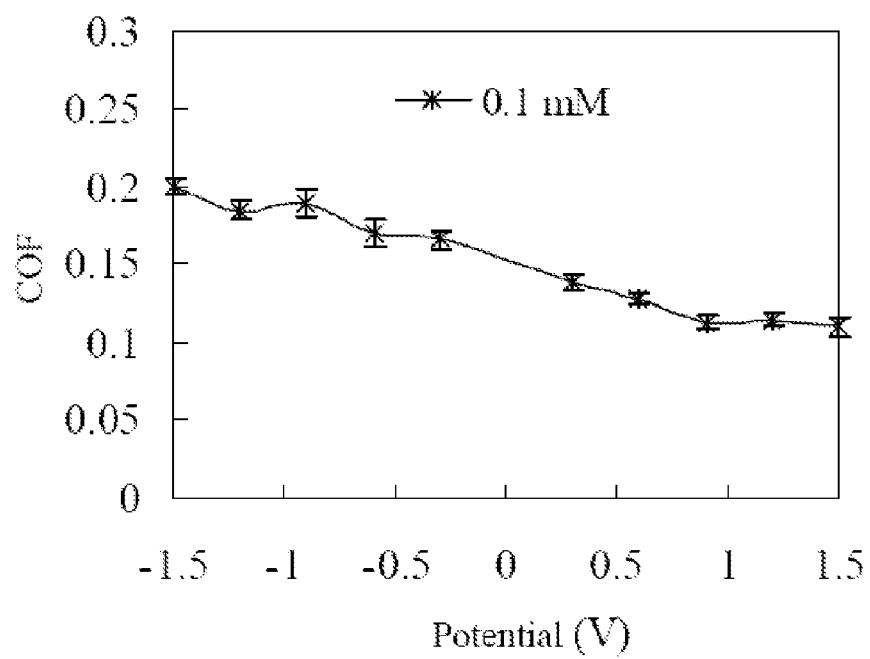
FIGS. 10 and 11 show curves illustrating the relationship between the potential of the working electrode and the friction coefficient according to a further embodiment of the present disclosure.
Figure 11:
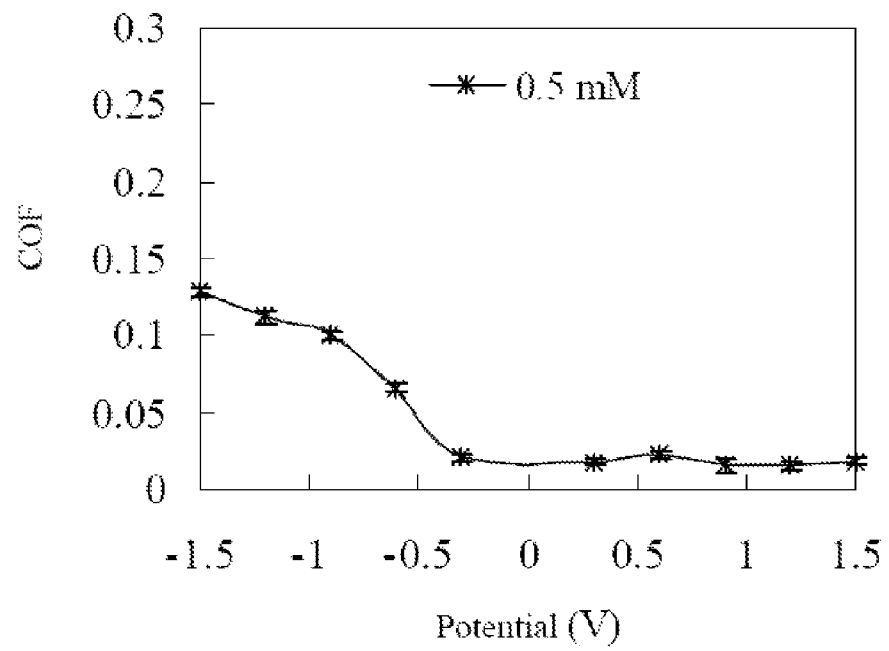

FIGS. 10-11 show curves illustrating how COF is changing with the change of the potential of the first friction part 1 under different lubricant concentrations. In the embodiment as shown in FIG. 10, the operating condition was as follows: a normal load of the friction pair was 50 N, a rotating speed of the friction pair was 10 rpm, a concentration of the sodium dodecyl sulfate was 0.1 mM based on the lubricant 4. In the embodiment as shown in FIG. 11, the operating condition was as follows: a normal load of the friction pair was 50 N, a rotating speed of the friction pair was 10 rpm, a concentration of the sodium dodecyl sulfate was 0.5 mM based on the lubricant 4.

COF under one potential was expressed as the average potential of the stable potential values under the one potential. Referring to FIGS. 10-11, COF increases when the potential moves toward the negative potential. Specifically, as shown in FIG. 10, when the concentration of the sodium dodecyl sulfate is 0.1 mM, COF is lower and remains unchanged substantially in a potential section ranging from +1.5 V to +0.9 V, and COF increases when the potential moves toward the negative potential in a potential section ranging from +0.9 V to −1.5 V. In addition, COF is lower and remains unchanged substantially in a potential section ranging from +1.5 V to −0.3 V, and COF increases when the potential moves toward the negative potential in a potential section ranging from −0.3 V to −1.5 V.

As described above, with the method according the embodiment of the present disclosure, with the change of the potential of the first friction part, lubricants covered on the metal friction parts (i.e. the first friction part) may change in the characteristics (such as subjected to a molecular rearrangement). In this condition, COF between the friction pair is changed. Therefore, COF may be controlled or adjusted precisely.

Embodiment 4

The method for controlling COF between the friction pair was carried out according to embodiments described above and was operated with the device shown in FIG. 1, and the relationship between COF and the rotating speed of the friction pair under different potentials was detected. In the present embodiment, the first friction part 1 was a stainless steel disc (022Cr17Ni12Mo2), the second friction part 2 was one $ZrO_2$ ball, and the lubricant 4 was a propylene carbonate solution containing sodium dodecyl sulfate.

Figure 12:
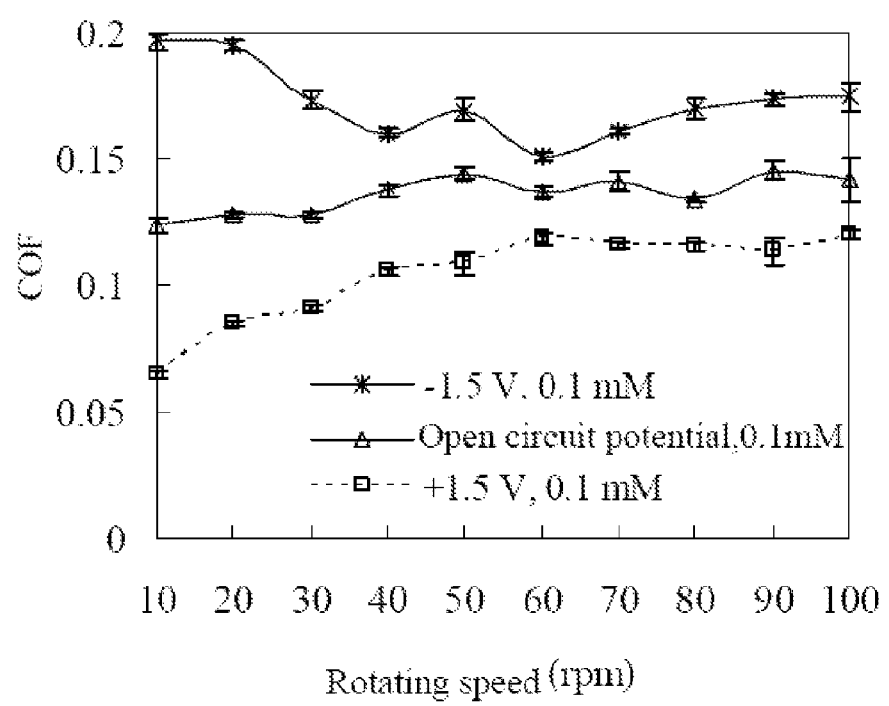
FIGS. 12 and 13 show curves illustrating the relationship between the friction coefficient and the rotating speed of the friction pair according to an embodiment of the present disclosure.
Figure 13:
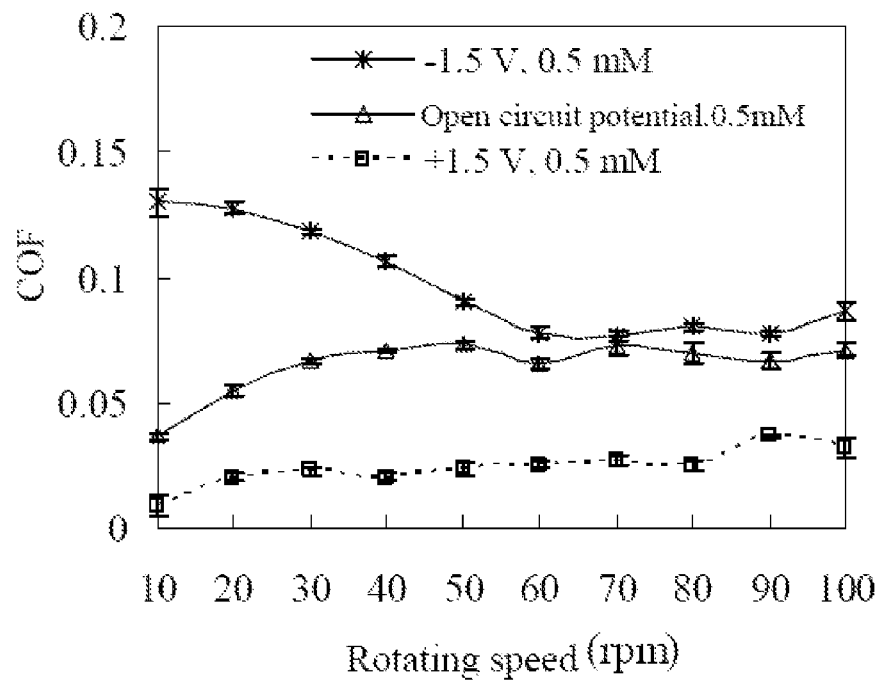

FIGS. 12-13 show curves illustrating how COF is changing with the change of the rotating speed of the friction pair under different potentials. In the embodiment as shown in FIG. 12, the operating condition was as follows: a normal load of the friction pair was 50 N and a concentration of the sodium dodecyl sulfate was 0.1 mM based on the lubricant 4. In the embodiment as shown in FIG. 13, the operating condition was as follows: a normal load of the friction pair was 50 N and a concentration of the sodium dodecyl sulfate was 0.5 mM based on the lubricant 4.

COF under one potential was expressed as the average potential of the stable potential values under the one potential. Referring to FIGS. 12-13, the first curve under the potential of −1.5 V is located above the second curve under the potential of +1.5 V, which indicates that the friction is well controlled within the rotating speed ranging from 10 rpm to 100 rpm.

As described above, with the method according the embodiment of the present disclosure, friction may be electrically controlled even in a wider rotating speed range, such as a rotating speed up to 100 rpm. In this way, various requirements need to be met in the electrically controlled friction fields may be satisfied.

Embodiment 5

The method for controlling COF between the friction pair was carried out according to embodiments described above and was operated with the device shown in FIG. 1, and the relationship between COF and the normal load of the friction pair under different potentials, as well as the relationship between the friction force and the normal load of the friction pair under different potentials were detected. In the present embodiment, the first friction part 1 was a stainless steel disc (022Cr17Ni12Mo2), the second friction part 2 was one $ZrO_2$ ball, and the lubricant 4 was a propylene carbonate solution containing sodium dodecyl sulfate.

Figure 14:
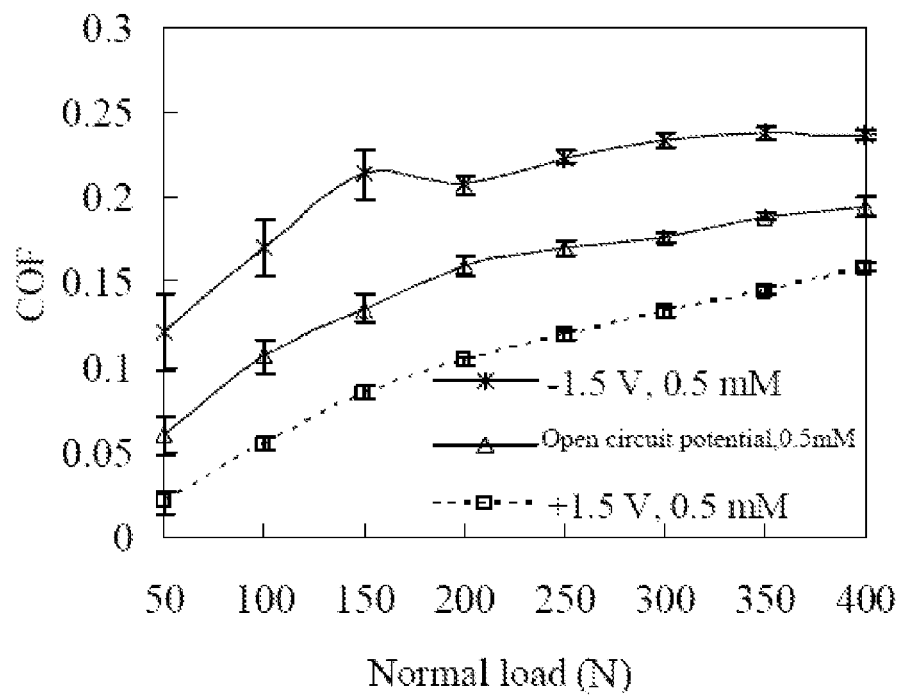
FIG. 14 shows a curve illustrating the relationship between the friction coefficient and the normal load of the friction pair according to an embodiment of the present disclosure.
Figure 15:
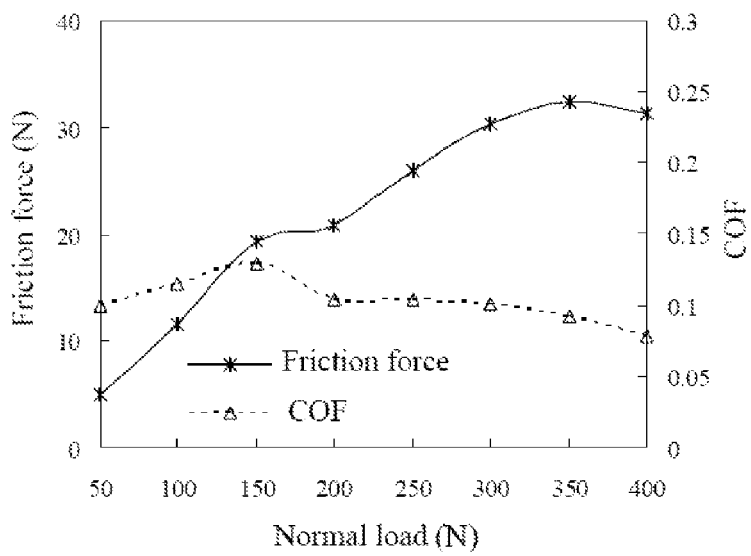
FIG. 15 shows a curve illustrating the relationship between the friction force and the normal load of the friction pair, as well as the relationship between the friction coefficient and the normal load of the friction pair according to an embodiment of the present disclosure.

FIG. 14 shows a curve illustrating how COF is changing with the change of the normal load of the friction pair under different potentials. FIG. 15 shows a curve illustrating how COF is changing with the change of the normal load of the friction pair under different potentials, as well as how friction force is changing with the change of the normal load of the friction pair under different potentials. In the embodiments as shown in FIGS. 14 and 15, the operating conditions were both as follows: a rotating speed of the friction pair was 10 rpm and a concentration of the sodium dodecyl sulfate was 0.5 mM based on the lubricant 4.

COF under one potential was expressed as the average potential of the stable potential values under the one potential. Referring to FIG. 14, the first curve under the potential of −1.5 V is located above the second curve under the potential of +1.5 V, which indicates that the friction is well controlled within the load ranging from 50 N to 400 N. As shown in FIG. 15, in the potential range of +1.5V→−1.5 V, COF change caused by the change of the potential maintains constant substantially under the load ranging from 50 N to 350 N, while the friction force increases with the increase of the normal load.

As described above, with the method according the embodiment of the present disclosure, friction may be electrically controlled even in a wider load range, such as a normal load up to 400 N. In this way, various requirements need to be met in the electrically controlled friction fields may be satisfied.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A method for controlling a friction coefficient between a friction pair, wherein the friction pair comprises a first friction part and a second friction part, and the method comprises:
   providing a lubricant between the first and second friction parts;
   applying a potential on the first friction part and adjusting the potential of the first friction part by an electrode system, in which the first friction part is used as a working electrode; and
   adjusting the friction coefficient by adjusting the potential of the first friction part,
   wherein the lubricant comprises propylene carbonate as a solvent and a surfactant,
   wherein the lubricant is a solution of sodium dodecyl sulfate in propylene carbonate, and the sodium dodecyl sulfate has a concentration selected from: 0.1 mM, 0.5 mM, 1 mM and 2 mM.

2. The method according to claim 1, further comprising subjecting the lubricant to an ultrasonication at a temperature ranging from 40° C. to about 50° C.

3. The method according to claim 1, wherein the first friction part is made of metal.

4. The method according to claim 1, wherein the second part is made of metal.

5. The method according to claim 1, wherein the second part is made of ceramic.

6. The method according to claim 1, wherein the potential is applied on the first friction part by an electrode system, and the electrode system comprises:
   a working electrode, wherein the first friction part is used as the working electrode;
   a counter electrode made from inert material and adapted to provide a current channel for the wording electrode; and
   a reference electrode adapted to provide a potential channel for the working electrode.

* * * * *